United States Patent [19]

Shamsuddin

[11] Patent Number: 5,348,860

[45] Date of Patent: Sep. 20, 1994

[54] SCREENING TEST AND KIT FOR CANCEROUS AND PRECANCEROUS CONDITIONS

[76] Inventor: Abulkalam M. Shamsuddin, 2916 Old Court Rd., Baltimore, Md. 21208

[21] Appl. No.: 776,786

[22] Filed: Oct. 15, 1991

Related U.S. Application Data

[63] Continuation-in-part of Ser. No. 228,268, Aug. 4, 1988, abandoned, and a continuation-in-part of Ser. No. 449,269, Dec. 12, 1989, Pat. No. 5,162,202.

[51] Int. Cl.$^5$ .................. C12Q 1/26; C12Q 1/54; C12Q 1/00
[52] U.S. Cl. .................................. 435/25; 435/14; 435/7.23; 435/967; 435/970; 435/975; 436/501; 436/518; 436/64; 436/94; 436/95; 436/813
[58] Field of Search ............. 735/7.1, 7.2, 7.23, 735/967, 970, 975, 14, 25; 436/501, 518, 64, 94, 95, 813, 815

[56] References Cited

U.S. PATENT DOCUMENTS

4,857,457 8/1989 Shamsuddin et al. ............. 435/7.23
5,162,202 11/1992 Shamsuddin ..................... 435/25

FOREIGN PATENT DOCUMENTS

0249418 12/1987 European Pat. Off. .

OTHER PUBLICATIONS

Howard, D. R., et al., "Carcinoma-associated cytostructural antigenic alterations: detection by lectin binding," *Cancer*, Jun. 15, 1981, 47(12) pp. 2872–2877, Abstract Only.

Kennedy, J. K., in *Bioactive Carbohydrates: In Chemistry, Biochemistry and Biology*, Ellis Horwood Limited, West Sussex, England, pp. 70–73, 1983.

Fairbanks, G., et al., Biochemistry, vol. 10, No. 13 pp. 2606–2616, 1971.

*Primary Examiner*—Toni R. Scheiner
*Attorney, Agent, or Firm*—Millen, White, Zelano, & Branigan

[57] ABSTRACT

An improved screening test method and kit for cancerous and precancerous conditions which is rapid, employs reagents which can be provided in kit form and which does not give false negatives due to sampling error, immobilizes a sample of a proteinaceous body fluid in a membrane filter, tests for marker carbohydrates therein which have vicinal galactose moieties and which are enzymatically oxidized with galactose oxidase to vicinal aldehydic moieties which then visualizes any thus-produced vicinal aldehydic moieties with Schiff's Reagent, then further oxidizes those samples which test negative for the marker carbohydrates with periodic acid, thereby rendering the sample visualizable with Schiff's Reagent if the sample contains glycoprotein, which applies the galactose oxidase directly to the membrane filter, thereby speeding up color developed, and employs Schiff's Reagent which was refrigerated after preparation until its color faded to a straw shade before being treated with activated charcoal, which treatment renders the solution storage-stable for many months and enhances its color development ability.

25 Claims, No Drawings

SCREENING TEST AND KIT FOR CANCEROUS AND PRECANCEROUS CONDITIONS

This is a continuation-in-part of U.S. patent application Ser. No. 07/228,268, filed Aug. 4, 1988, now abandoned, and U.S. patent application Ser. No. 07/449,269, filed Dec. 12, 1989, now U.S. Pat. No. 5,162,202.

BACKGROUND OF THE INVENTION

This invention relates to a screening test for cancerous and precancerous conditions and to a kit containing the components necessary for conducting the test.

Cancer is a major public health problem in the world. Even as pharmaceutical agents for the treatment of cancer are developed, early detection and prevention are still the best hope for combating this human tragedy. In U.S. Pat. No. 4,857,457 I claim and in Shamsuddin et al., Human Pathology, 19: 7-10, 1988, there is reported a screening test for colorectal cancer which can detect cancer of the large intestine employing rectal mucus. The mucus is reacted with the enzyme galactose oxidase by moistening a cellulose membrane filter, which had previously been impregnated with a phosphate buffer solution of the enzyme and then lyophilized, and then contacting the moistened cellulose membrane filter with a Metricel membrane filter bearing the mucus sample for 1-2 hours. The mucus-bearing membrane filter is then washed with distilled water for 1 minute, reacted with basic fuchsin for 15 minutes, washed in tap water for 10 minutes and then air dried.

This basic procedure, although simple, is limited to detecting rectocolon cancer and precancerous conditions. Moreover, it suffers from the serious deficiency that it has since been found by me that it is not specific to cancers of the large intestine, i.e., the marker disaccharide employed therein as predicative of rectocolon cancer is also present in rectal mucus when a cancerous or precancerous condition is present at another site of the body. Also the test as described therein is lengthy. Moreover, if a patient tests positive in this screening test, rather than being selectively predictive of rectocolon cancer, it in fact is predictive of virtually any cancerous or precancerous condition. If a patient tests negative by this screening test, it can mean either a biological negative, i.e., the patient does not have a cancerous or precancerous condition which releases a marker carbohydrate employed in the screening test, or it is technically negative, i.e., and insufficient mucus from the rectum was obtained in order to detect any marker carbohydrate present therein. The latter situation could mean a "false negative," the consequence of which could be dangerous to the person tested since any cancer present could continue to grow undetected because the negative results would give the patient and the patient's physician a false sense of security which might cause the patient or his/her physician to disregard symptoms that might otherwise be investigated if the negative results had not been obtained.

Another deficiency of this test is the known unstable nature of the basic fuchsin which is a critical component therein. According to the prior art, basic fuchsin must be prepared fresh and discarded after a week because of its instability. (Manual of Histological Staining Methods of the Armed Forces Institute of Pathology, Ed. 3, McGraw-Hill, New York, 1968, p. 159.) This makes it impossible to provide the materials required to conduct the screening test in kit form, since shipping, handling and storage of such kits would require a shelf life of at least six months and the instability of the basic fuchsin would preclude such a shelf life.

Finally, as noted above, the screening test as reported by me, Shamsuddin et al., Human Pathology, 1988, 19:7-10, in addition to the several hours of preparation for the lyophilization of galactose oxidase, employed more than two hours to obtain the results thereof, which makes the test impractical for mass screening of large segments of the population and effectively precludes reporting the test results to the individual tested before that individual leaves the test area, e.g., the doctor's office or a mobile laboratory.

Since most cancers in humans are believed to be the result of exposure to one or more environmental carcinogens which are excreted through the large intestine or urinary bladder, it can be expected that the carcinogen(s) and/or their metabolite(s) cause changes in those organs, in addition to causing corresponding changes simultaneously in the organ bearing the cancer and precancer. Precancer or precancerous conditions are those stages or diseases that render an individual highly susceptible to subsequent cancer (high risk symptomatic). Based on this hypothesis the presence of or threat of a cancerous or precancerous condition in the body of an individual, including but not restricted to the large intestine, can be detected accurately by the method of this invention initially using rectal mucus sampling, followed, if necessary, by sampling of other body fluids, such as secretions of breast, prostate, semen, uterine endocervix and vagina, mucus, sputum, bronchial or alveolar secretions, until the precise situs of the cancerous or precancerous condition is located, without the prior risk of false negatives which limited the value of this technique as a screening test, particularly as a field test, for the general population. The present invention eliminates false negative results which are obtained as a result of inadequate sampling, permits rapid testing for the presence of absence of precancer or cancer carbohydrate markers in about 15 minutes or less and ensures the stability of the critical components required to conduct the test for over one year. It also eliminates the "false positives" of U.S. Pat. No. 4,857,457, i.e., a positive test supposedly indicating a cancerous or precancerous condition in the rectocolon area but in fact is present in another area of the body.

OBJECTS OF THE INVENTION

It is a general object of the invention to provide a screening test for cancerous and high risk symptomatic precancerous conditions that does not suffer from the above-described deficiencies of the prior art test.

A more specific object of the present invention is to provide a novel screening test for cancerous and precancerous conditions which eliminates the error of technically false-negative results.

Another object of the invention is to provide such a test which can be performed rapidly, thereby facilitating its use in mass testing programs which do not require a special diagnostic laboratory and permitting reporting the results of the test to the individual or individuals tested (or their physician) and/or obtain an additional rectal mucus sample if a negative result is determined to be a false negative, before the individual leaves the testing area.

Yet another object is to provide such a kit.

Still another object of the invention is to provide a kit for conducting the screening test of this invention whose critical components are stable for a protracted period.

Still another object is to provide a method for performing the screening test employing the kit of this invention which can be completed fast enough to provide results for the tests to the individuals being tested while they wait.

Yet another object is to provide a method of preparing Schiff's Reagent, a component of the kit of this invention, which gives a much stronger color reaction and is storage-stable for many months, thereby rendering the kit commercially feasible for field testing.

Upon further study of the specification and appended claims, further objects and advantages of this invention will become apparent to those skilled in the art.

SUMMARY OF THE INVENTION

In a testing method aspect, this invention relates to a method for testing a human being for a cancerous and precancerous condition which comprises the steps of (a) obtaining a sample of rectal mucus from an individual; (b) assaying, e.g., with galactose oxidase followed by basic fuchsin, the sample of rectal mucus for the presence therein of at least one of the marker carbohydrates beta-D-Gal-(1->3)-D-GalNAc, Fuc-alpha-1->2-Gal-beta-(1->4)-Fuc-alpha-1->3-GlcNAc, Fuc-alpha-1->2 Gal-beta-(1->4)-Fuc-alpha-1->3 GlcNAc-beta-(1->3)-Gal-beta-(1->4)-GlcNAc and Fuc-alpha-1->2-Gal-beta-(1->4)-Fuc-alpha-1->3-GlcNAc-beta-(1->3)-Gal-beta-(1->4)-Fuc alpha-1->3-GlcNAc, (c) subjecting a sample which tests negative in that assay, either simultaneously employing a separate portion of the mucus sample or sequentially employing the same portion of the mucus, to oxidizing conditions which are capable of oxidative ring opening of any saccharide present in the sample at a hydroxy group-bearing ring carbon atom thereof to form an aldehydic sugar moiety, e.g., with periodic acid; and (d) then assaying the thus-oxidized sample for the presence of any aldehydic sugar moieties formed in the thus-oxidized sample, the presence of thereby formed aldehydic sugar moieties confirming the adequacy of the mucus sampling, and the absence therein of thereby formed aldehyde sugar moieties establishing that the negative test results were due to mucus sampling error.

In a preferred method aspect the method is conducted in the field concurrently on a plurality of rectal mucus samples obtained from a plurality of human beings and in 10 a preferred aspect of this field testing embodiment of the invention, the rectal mucus of only those individuals which test positive in step (b) are tested in accordance with steps (c) and (d).

In a diagnosis aspect of this invention, an individual whose rectal mucus tests positive in step (b) is medically examined for a cancerous or precancerous condition of the rectum and colon and, if none is found, the testing method of this invention is repeated, on mucus or other proteinaceous fluid associated with another organ of the individual, for a cancerous or precancerous condition of that organ, e.g., prostatic secretion or semen in males, vaginal and endocervical mucus and breast secretion in females, and sputum, bronchial and alveolar secretions in both males and females. A positive test result with one of these fluids is very strong evidence that the positive result obtained with the rectal mucus is the result of a cancerous or precancerous condition in an organ associated with that other fluid.

In an article of manufacture aspect, this invention relates to a diagnostic kit for detecting a cancerous or precancerous condition in human beings according to the test method of this invention which comprises galactose oxidase; a water-insoluble support capable of absorbing rectal mucus; and a storage-stable solution of basic fuchsin.

In a preferred embodiment, the kit also comprises a chemical oxidant capable of oxidative ring opening of the cyclic sugar moieties of any saccharide present in the sample at a hydroxy group-bearing ring carbon atom thereof to form an aldehydic sugar moiety, i.e., periodic acid.

In a process aspect, this invention relates to a process for producing an aqueous solution of basic fuchsin suitable for use in the kit and method of this invention wherein a basic solution of fuchsin and a bisulfate is treated with activated charcoal and is stored at below room temperature before the activated charcoal is removed therefrom, the improvement which comprises storing the basic solution at below room temperature until the color thereof fades to a straw color before the activated charcoal is added thereto, thereby rendering the solution storage-stable and enhancing the color development ability thereof.

DETAILED DISCLOSURE

Specific embodiments of the technique employed in this invention for detecting the presence of the marker carbohydrates in the rectal mucus of individuals tested for cancerous or precancerous conditions is disclosed in U.S. Pat. No. 4,857,457 and in prior U.S. patent application Ser. No. 07/228,268, filed August 4, 1988, of which I am one of the inventors. The assay method as disclosed in this patent, however, is slow, i.e., several hours were employed using the galactose oxidase strip test of Example 3 thereof to obtain the results thereof. Moreover, there is no teaching therein of how one could confirm the adequacy of sampling when the test reaction is negative or how to conduct the test in the field employing a kit containing a Schiff's Reagent which is storage-stable for many months, a fundamental requirement of a commercial kit containing a Schiff's Reagent.

This invention provides a reliable diagnostic tool for the detection of a wide variety of cancers, e.g., rectal, colon, blood, lymph node, stomach, kidney, gall bladder, prostate, testes, breast, cervix and ovaries. In precancerous conditions, i.e., those in which the individual is high risk symptomatic, i.e., is in a "highly susceptible to subsequent cancer" catagory.

The present invention is an improvement in the assay as described therein, with respect to eliminating the false positives which are obtained if the assay is used to screen for rectocolon cancer, with false negative results, which are obtained as a result of sampling error, with respect to speed and with respect to the stability of the Schiff's Reagent which is employed therein, the latter feature making feasible the production of a kit which can be sold commercially for widespread use because no reagent has to be made up immediately prior to using the kit.

With respect to the many false positives which are obtained when the method of U.S. Pat. No. 4,857,457 is used to diagnose rectocolon cancer, it was later discovered that the test procedure employed therein, instead of being selectively predictive of rectocolon cancer, actually is a reliable assay for a variety of cancerous and precancerous conditions as discussed hereinafter, apparently because the aberration in the individual's metabolic processes which occurs when the individual has a cancerous or precancerous condition also results in one or more of the marker saccharides identified hereinafter being present in the rectal mucus of that individual. Thus, according to the present invention, the procedure of U.S. Pat. No. 4,857,457, which is only poorly selectively predictive of rectocolon cancer, is employed to accurately detect a variety of cancerous and precancerous conditions.

With respect to the false negatives which invariably occur as a result of sampling error when practicing the method of U.S. Pat. No. 4,857,457 (or any other method involving obtaining a sample of body fluid or tissue), these are eliminated in the method of this invention by further testing the rectal mucus sample, if it assays negative according to the procedure of U.S. Pat. No. 4,857,457, for the presence of any saccharide therein oxidizable, to an aldehydic sugar moiety, which latter test, if positive, verifies the presence of an adequate amount of rectal mucus in the sample to detect the marker protein and verifies that the individual tests negative and, if negative, establishes that it is a false negative.

With respect to the kit aspect of this invention, it was discovered, surprisingly, that if the generally accepted technique for producing the Schiff's Reagent of mixing the reagent after preparation with activated charcoal and then refrigerating is not followed, a solution which is storage-stable for months at room temperature can easily and reproducibly be produced. This method renders the color reaction more intense than is obtained with conventional Schiff's Reagent. According to the technique of this invention, the Schiff's base is first refrigerated in the absence of activated charcoal, e.g., at about 0°–15° C., preferably about 0°–10° C., until the color thereof fades to a straw shade, e.g,. for 1, 2 or more days usually about 48 hours. After the solution has faded to a straw color, it is then treated with activated charcoal or like surface-active absorbent, e.g., with stirring, e.g., at room temperature for from about a few minutes to several hours or days. After removing the charcoal, e.g., by filtration, the Schiff's Reagent is filled into a vial or bottle of a volume suitable for conducting the number of tests for which the kit is designed, e.g., 1, 5, 10, 50, 100 or more.

In another aspect of this invention, the detection method is used to field test a plurality of individuals for any cancerous or precancerous condition. When conducting the steps thereof, preferably only those samples which assay negative for a marker saccharide is further tested for any saccharide. Alternatively, each sample can be divided into two portions, the first of which is assayed for a marker saccharide and the latter is assayed for any other saccharide oxidizable to an aldehydic sugar moiety, thereby permitting the diagnostic procedure and the false negative tests to be conducted concurrently and thereby further shortening the time period required to be able to report a biologically negative test result.

With further respect to the speed aspect of this invention, the assay for a marker saccharide can be conducted far more rapidly than was apparent from U.S. Pat. No. 4,857,457 and in my publication in *Human Pathology, supra,* as evident from the Example hereinafter, the whole testing procedure including the test for false negatives, can be completed in less than one-half hour, e.g., within about 15–20 minutes after collection of the rectal mucus sample. This enables the testing physician or laboratory to report the results of the test (or take another sample if a biological negative result is obtained) before the individual leaves the testing area.

A marker saccharide in a rectal mucus sample is detected by selective oxidation of the glycoprotein in the mucus sample with galactose oxidase or comparable oxidant which will oxidize the primary hydroxy groups of only the galactose moieties in the saccharides present in the glycoprotein into aldehydic groups. The resulting aldehydic groups can then be visualized with a Schiff's Reagent, e.g., basic fuchsin which forms a magenta color.

The galactose moieties marker saccharides are rapidly selectively oxidized at room temperature with galactose oxidase to aldehydic sugar moieties, e.g., in less than about 15 minutes, e.g., about 5–10 minutes, and even more rapidly at elevated temperatures, up to the deactivation temperature of the enzyme. The ratios of enzyme to substrate and vehicles suitable for activating the enzyme which are well known in the art when using this enzyme can be employed.

The oxidized sample, with or without first removal or inactivation of the galactose oxidase is then treated with a reagent which visualizes or permits visualization of the thus-produced aldehydic sugar moieties, e.g., fuchsin, rosaniline, magenta or other Schiff base decolorized dye.

The marker carbohydrates can be assayed by selective oxidation of a galactose moiety therein with galactose oxidase followed by visualization of the thus-produced aldehydic saccharide with basic fuchsin. They can also be assayed employing an agglutination inhibition test, e.g., using an approximately stoichiometric amount of peanut agglutinin, by detecting the presence of biotinylated peanut agglutinin and detecting the complex by reacting it with avidin which is conjugated with one of the marker carbohydrates (saccharides).

A marker saccharide in a rectal mucus sample can also be detected by agglomeration of sensitized beads.

The objects, features and advantages of the present invention are attained in one aspect thereof by providing a rapid, reliable with respect to false negatives and commercially feasible method for detecting the presence of a precancerous or cancerous condition in a human. The invention employs a test method which comprises obtaining a sample of rectal mucus, assaying the sample to detect the presence therein of at least one of the marker carbohydrates beta-D-Gal-(1->3)-D-GalNAc. Fuc-alpha-1->2-Galbeta-(1->4)-Fuc-alpha-1->3-GlcNAc, Fuc-alpha-1>2-Galbeta-(1->4)-Fuc-alpha-1->3-GlcNAc-beta-(1->3)-Gal-beta-(1->4)-GlcNAc or Fuc-alpha-1->2-Gal-beta-(1->4)-Fucalpha-1->3-GlcNAc-beta-(1->3)-Gal-beta-(1->4)-Fuc-alpha-1->3-GlcNAc; and, optionally, diagnosing the presence and degree of precancer or cancer based upon the amount of the marker carbohydrate(s) detected in the rectal mucus. Except for the modifications thereof of this invention which renders the test procedure rapid, reliable as to false negatives and commercially feasible, the test methods are those disclosed in U.S. Pat. No. 4,857,457 and prior filed U.S. patent application Ser. No. 07/228,268, filed Aug. 4, 1988, which disclosures are incorporated herein by reference.

In one embodiment, the assay may be performed by reacting the body fluid with a precise amount of peanut agglutinin or other specific binding moiety for the saccharide and then detecting the presence of unbound moiety. The reactant moiety can be immobilized onto a water-insoluble support, such as a membrane filter or solid beads of latex, plastic, glass, etc. In order to increase the sensitivity of the method, the reactant moiety can first be biotinylated in a conventional manner.

The complex can be detected by any of various suitable techniques, either directly or indirectly, e.g., immunologically, enzymatically, oxidative-reductively etc. Presently, preferred is the formation of a complex with avidin conjugated to a suitable marker, e.g., fuchsin or other dyes, radioactive labelling, fluorescent dyes such as fluorescein isothiocyanate or Rhodamine B, luminescent dyes such as luciferol, luminol, biotin, etc.

The presence of the disaccharide beta-D-Gal-(1->3)GalNAc is readily detected by agglomeration of sensitized beads which have been coated with PNA, e.g., glass, agarose, polystyrene, latex, etc. A preferred method for detecting the presence of the complex is by selectively oxidizing the galactose moiety of the saccharide to an aldehydic disaccharide, e.g., with galactose oxidase, and detecting the presence of the thus-oxidized aldehydric sugar moiety.

In a kit embodiment of the invention, a kit is provided which comprises separate containers of galactose oxidase, a protein-capturing membrane filter, storage-stable basic fuchsin and, optionally, periodic acid, and deionized distilled water. Preferably, the galactose oxidase is encapsulated or is impregnated into the same membrane filter onto which the mucus sample is applied. The pressure of smearing the mucus sample on the membrane filter is sufficient to activate the enzyme. The marker carbohydrate is then visualized by staining with the Schiff's base, e.g., basic fuchsin.

In one aspect, the assay test detects specific biochemical changes in rectal (large intestinal) mucus associated with a cancerous condition, e.g., of the large intestine, which results in the production of the disaccharide beta-D-Gal-(1->3)-D-GalNAc, also known as T-antigen, which is absent in the body fluids of normal individuals but is present in the rectal mucus of individuals with at least some cancerous and precancerous conditions. Shamsuddin et al. developed various techniques for the detection of this sugar moiety in a simple and inexpensive manner (but not as rapidly as the method employed in this invention or which permits the use of storage-stable fuchsin or which eliminates false negatives), which techniques can be used to screen individuals for large intestinal diseases generally, including cancer.

The lectin, peanut agglutinin (PNA) specifically binds with T-antigen and causes agglutination of T-antigen activated RBC. Exploiting these characteristics of PNA, initially a simple inhibition assay has been developed wherein T-antigen in a body fluid sample will bind with PNA and, therefore, PNA will not react with RBC and the red cells will accordingly not agglutinate. This test is very simple and can be performed rapidly. Using microtiter plates, a large number of samples can be screened in a short time. The galactose oxidase test can be done conveniently on a strip of membrane filter.

Because not all cancerous and precancerous conditions generate all of the marker carbohydrates identified herein in the same proportions, in one embodiment of this invention more than one of the assay tests described herein is used to test a plurality of samples of the rectal mucus and/or other proteinaceous bodily fluids of an individual being screened for a specific cancerous or precancerous condition.

In addition to cancerous conditions, the tests used in methods of this invention can detect other diseases of the colon including those that carry a high risk of cancer such as polyps, fistula, ureterosigmoidostomy, Crohn's disease, and ulcerative colitis.

In one embodiment, the rectal mucus is tested for the marker carbohydrates as first step screening test for the presence of any cancerous or precancerous condition. If the screening test is positive, other proteinaceous body secretions easily accessed by non-invasive methods would be tested as a second step as a diagnostic method for targeting a cancer in a specific organ.

Other properties, such as immobilization of PNA onto a water-insoluble support, immunological detection of the glycoconjugate or oxidation of the sugar moiety and detection by dyes, radio-chemicals, etc., can be exploited to develop additional assays. The use of an antibody directed against this sugar moiety in an immunoassay enables accurate estimation and monitoring of this moiety in rectal mucus as well as other body fluids. In the immunoassay, the antibody can be tagged by a radioactive fluorescent or other suitable label for quantitative or semiquantitative detection.

Avidin, a glycoprotein (67,000 MW), has an extraordinarily high affinity for the vitamin biotin. Inasmuch as biotin molecules can be coupled to various proteins (biotinylation), avidin can be conjugated with various markers such as enzymes, dyes, heavy metals, radioactive isotopes, etc. Avidin has four binding sites for biotin, and many biotin molecules can be incorporated on a given protein. This amplification principle can be useful to detect minute amounts (i.e., ng/ml or even pg/ml) of the marker disaccharides in the glycoproteins of rectal mucus obtained during digital rectal examination. Mucus glycoprotein containing the specific disaccharide will avidly bind to the lectins immobilized on a solid phase. A matrix formed by biotinylated lectins and enzyme-avidin D conjugate will bind to residual disaccharides on the immobilized glycoprotein lectins, while a suitable substrate will amplify the reaction.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight. The entire disclosures of all applications, patents and publications, if any, cited above and below, and of corresponding applications, are hereby incorporated by reference.

In all of the tests described herein, sterile gloves should be worn; forceps, scissors, and all work surfaces should be scrupulously clean, membrane filters should be handled with forceps and filters must not be contaminated (even saliva may contaminate).

Use of Galactose Oxidase Strip Test For Primary Screening

This technique uses the ability of galactose oxidase to selectively oxidize the C-6 hydroxyl group of galactose moieties of the glycoprotein in the mucus, e.g., both the galactose and N-acetyl galactosamine residues of the beta-D-Gal-(1->3)-D-GalNAc to D-galactohexodialdose. The presence of aldehyde sugar moieties in this thus-oxidized product is evidence of a marker carbohydrate in the glycoprotein. Their presence can be detected using Schiff's Reagent, e.g., basic fuchsin.

A mucus sample is obtained by digital examination of the rectum of a test individual with the gloved index finger. The mucus on the examining finger is smeared on the scored side of a piece of membrane filter (e.g., Metricel membrane filter 0.45 μm, Gelman Sciences, Inc., Ann Arbor, Mich. 48106). An appropriate amount (depending on the size of the filter paper) of galactose oxidase is applied directly to the filter. After about 5–10 minutes reaction time, usually at room temperature, wash the membrane for 1 minute in deionized water and then place the membrane in Schiff's Reagent for 1 minute and then wash the membrane for 1 minute in running tap water. Shake off excess water and dry the membrane by air drying or in an oven. A bright magenta coloration of the mucus smear when completely dried indicates a positive test.

With typical results, no false negatives and far fewer false positives (less than 10s o vs. about 95%) are found than in the conventional fecal occult blood test for cancer of the colon. A sample giving a negative result is then tested in accordance with this invention for glycoprotein content by oxidation with periodic acid followed by treatment again with a Schiff's Reagent. Development of a magenta color confirms that the negative result is a biological negative and not a false negative due to sampling error. Because the whole procedure requires less than one-half hour, a second sample can conveniently be obtained from an individual whose first sample yielded a false negative.

Use of Galactose Oxidase Strip Test for Diagnosis Testing

Obtain, from an individual whose rectal mucus tested positive in the above-described galactose oxide screening test but was determined by medical examination to be free of cancer or a precancerous condition in the rectal-large intestine area, a sample of a proteinaceous fluid from another organ, e.g., vaginal mucus or discharge from the breast if the patient is female, seminal fluid from a middle aged or geriatric male or sputum from a patient exhibiting one or more abnormal respiratory symptoms. Test the sample of fluid in the same manner as for the rectal mucus sample and, if positive, focus the medical examination on the organ associated with the tested fluid and, if negative, repeat the test on a sample of fluid from another organ.

Galactose Oxidase Strip Test Kit

The simple use test kit is packaged in a conventional manner in a cardboard carton containing (a) a capped vial containing an amount of storage-stable basic fuchsin, prepared according to the preparation hereinafter, sufficient to saturate twice (b) a strip of membrane filter (Metricel membrane filter 0.46 μm, Gelman Sciences, Inc., Ann Arbor, Michigan). Also present in the kit is (c) an amount of a storage-stable form of galactose oxidase which is present in the kit in a sealed capped bottle impregnated in the strip of membrane filter in an amount sufficient to oxidize marker carbohydrates in the sample. Also present are (d) periodic acid, and (e) a color chart for comparison with the test result and interpretation thereof.

For field testing purposes, the kit contains a plurality of the membrane filters strips, e.g., 5, 10, 50, 100 or more and the amounts of galactose oxidase, buffer solution and basic fuchsin solutions are increased proportionately.

PREPARATION

Storage-Stable Schiff Reagent Solution

Dissolve 1.0 gm of basic fuchsin in 200.0 ml of hot distilled water and bring to the boiling point. Cool to 50° C., add 20.0 ml of I N HCl and cool further and add 1.0 gm of sodium metabisulfate. Refrigerate in the dark until the solution becomes straw colored (about 48 hours). Then add 5 g of activated charcoal, thoroughly stir and remove the charcoal by filtration. The clear filtrate is a Schiff's Reagent which is storage-stable for many months, e.g., at least one year. Moreover, the magenta color which is produced therewith is more intense than that obtained with conventionally prepared Schiff's Reagent.

EXAMPLES

Following the procedure described above for the galactose oxidase strip test, the rectal mucus of 382 individuals either with known cancerous or precancerous conditions of the large intestine or other body site or who were asymptomatic. The term "other body site" includes, but is not restricted to, the uterine cervix, kidneys, head and neck, uterine cervix, ovaries, breast, lymph nodes, blood, stomach, testes prostate, longs, gall bladder, liver and pancreas.

TABLE 1 summarizes the results of these tests.

| Large Intestinal | | Other Body Site | High Risk | |
|---|---|---|---|---|
| Cancer | Polyp | Cancer | Symptomatic | Normal |
| 31/34 | 53/85 | 10/16 | 95/190 | 3/57 |
| 91.2% | 63.5% | 62.5% | 50% | 5.2% |

The data in the first line are the number of individuals tested positive/total number of individuals in each category. Note that only 5% of the apparently normal (asymptomatic) individuals elicited a positive reaction.

In accordance with this invention, the mucus sample of each individual was obtained by digital rectal examination with the gloved finger lubricated with either normal saline or other common lubricants used for such procedure. The mucus on the examining finger was smeared on the protein-capturing membrane filter, reacted with galactose oxidase for 10 minutes at ambient temperature (25° C.), washed with deionized distilled water, reacted with basic fuchsin for 1 minute and then washed in tap water for 1 minute. The presence of a cancerous or precancerous condition is indicated by the magenta coloration of areas of the sample. Each sample which tested negative in this test by the absence of magenta coloration was then reacted with periodic acid for 5 minutes, washed with deionized distilled water and reacted again with basic fuchsin for 1 minute and washed with tap water. The positive reaction eliciting a purple to magenta color is indicative of the fact that mucus glycoprotein had indeed been obtained but is negative with respect to the presence therein of a marker carbohydrate. The absence of magenta coloration means sampling error and the individual is tested again with a fresh mucus sample.

In a separate independent study employing the above techniques, the presence of 9/11 stomach cancers, 4/4 cancers of the liver, gall bladder, common bile duct and pancreas were signaled by a positive test with the rectal mucus, galactose oxidase and basic fuchsin and, in the same manner, in another study, 12/18 patients with cancers of the stomach, pancreas and liver gave positive test results. In other studies, the rectal mucus of individuals with cancer of the ovary, breast or stomach tested positive for a marker protein.

Contemplated equivalents of the method of this invention is the use thereof as a primary screening test employing seminal fluid, breast discharge or vaginal mucus for the detection of cancerous or precancerous conditions of the prostate, of the breast and of the cervix and/or ovaries, respectively, and the use of another galactose moiety specific oxidant instead of galactose oxidase.

Hemagglutination Inhibition Test

This standard hemagglutination inhibition test, e.g., as described in U.S. Pat. No. 4,857,457, can be used in the marker carbohydrate test employed in this invention.

In typical results with this test, no false negatives and far fewer false positives (about one-third vs. about 95) are obtained than in the conventional fecal occult blood test. A negative test result is checked for proper mucus sampling procedure by testing the sample for glycoprotein content according to this invention.

Latex Agglutination Test

In this test, 500 $\mu$l of suspended latex beads (15.8 $\mu$ diameter, Sigma Chemical Co., St. Louis, Mo.) are centrifuged at 3,000 RPM for 15 seconds and the supernatant is decanted. 500 $\mu$g of lectin, e.g., PNA (Vector Laboratories Ltd., Burlingame, Calif.), is dissolved in 500 $\mu$l of carbonate buffer (pH 9.6) and added to the pellet of latex beads. The pellet is resuspended and incubated at 25° C. for 2 hours with occasional mild shaking to resuspend the beads and allow a more uniform binding. After incubation, the sample is centrifuged at 3,000 RPM for 15 seconds the supernatant decanted, and the pellet resuspended in PBS (pH 7.4). Any unbound PNA is washed off by repeating the previous step three times. The final pellet is suspended and diluted 1:10 in PBS.

For testing a mucus sample collected during digital rectal examination, 10 $\mu$l of mucus in PBS is added to an equal amount of the latex beads and placed on a glass slide. After five minutes of incubation at 25° C., the slide is read. An agglutination of the beads, indicating the presence of the marker disaccharide is read as positive for a cancerous condition, whereas no agglutination after 5 minutes indicates either the absence of the disaccharide and hence a cancer-free status or sampling error. The latter possibility is eliminated in accordance with this invention by assaying the mucus sample for glycoprotein content.

Biotinylated Lectin Avidin-Enzyme Assay

Plant lectins, e.g., PNA dissolved in carbonate buffer (pH 9) to a final concentration of 100 ng/ml is used to cot the microtiter wells. 10 ng of lectins in 100 $\mu$l buffer are placed in each well and incubated at 37° C. for 2 hours. The wells are then washed off with phosphate buffered saline (PBS) pH 7.4, after which 100 $\mu$l of test mucus (dissolved in PBS) is added to the microtiter wells and the mixture is incubated at 37° C. for 1 hour. The wells are then washed three times with PBS to remove 100 $\mu$l of unbound mucus. Biotinylated lectins (1 $\mu$g/ml) is incubated for an additional hour at 37° C. in order to bind with residual marker carbohydrate (if any). The wells are washed three times with PBS to wash off unbound biotinylated lectins. Avidin-D-alkaline phosphatase (Vector Corporation, Burlingame, Calif.) is then added (100 $\mu$l/well, 1:50 dilution) to the wells and incubated for 1 hour at 37° C. Following 2 washed with PBS and 3 washes with bicarbonate buffer (pH 9.8), the substrate p-nitrophenyl phosphate (1 mg/ml) is added to the wells (100 $\mu$l/well). Optical absorbance at 405 nm is read after 30 minutes incubation at 37° C. Mucus from known cancer patients give position results while mucus from non-cancer patients give negative results. In the event of a negative result, the adequacy of sampling is confirmed in accordance with this invention, e.g., with periodic acid followed by fuchsin.

The preceding examples can be repeated with similar success by substituting the generically or specifically described reactants and/or operating conditions of this invention for those used in the preceding samples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A screening method for rapidly testing a human being for a cancerous or precancerous condition and as part of the same testing eliminating the possibility of a false negative, whereby the individual can be immediately retested if a negative assay is due to procedural error, which comprises the steps of (a) obtaining a sample of rectal mucus from an individual; (b) assaying a portion of the sample for the presence therein of glycoprotein containing at least one carbohydrate selected from the group consisting of beta-D-Gal-(1->3)-D-GalNAc, Fuc-alpha-1->2 Gal-Beta(1->4)-Fuc-alpha-1->3-GlcNAc, Fuc-Alpha-1->2 Gal-beta-(1->4)-Fuc-alpha-1->3-GlcNAcbeta-(1->3)-Gal-beta-(1>4)-GlcNAc and Fuc-alpha-1->2-Gal-beta-(1->4)-Fuc-alpha-1->3-GlcNAc-beta-(1->3)-Gal-beta-(1->4)-Fuc-alpha-1->3-GlcNAc, by briefly subjecting the sample to oxidizing conditions which are capable of selectively oxidizing only the cyclic sugar moieties of any said marker carbohydrate present in the glycoprotein in the sample at a hydroxy group-bearing ring carbon atom thereof to form an aldehydic sugar moiety and then visualizing any aldehydic saccharide groups thus formed with a Schiff's base decolorized dye; (c) also assaying a portion of the sample for the presence therein of any glycoprotein by subjecting the sample to the oxidizing action of an oxidizing agent which oxidizes the saccharide moieties of any glycoprotein therein to aldehydic sugar moieties and then visualizing any thus-produced aldehydic sugar moieties, the presence of thereby formed aldehydic sugar moieties confirming the adequacy of the mucus sampling and the absence therein of thereby formed aldehyde sugar moieties establishing that the negative test results were due to mucus sampling error; and (d) either retesting the individual in the same manner with a fresh sample of rectal mucus, if the first sample assays negative in steps (b) and (c), or examining another proteinaceous fluid associated with another organ of the individual in the same manner, if the rectal mucus sample tests positive and no abnormality of the rectum or colon is found.

2. A method according to claim 1, wherein the assay comprises the steps of adsorbing the mucus sample onto a protein-capturing water-insoluble substrate and then washing the substrate to remove non-immobilized components of the mucus sample from the substrate.

3. A method according to claim 2, wherein the insoluble substrate is a membrane filter.

4. A method according to claim 1, wherein the marker carbohydrate sugar moieties are assayed by selectively oxidizing the glycoprotein so as to selectively oxidize the primary hydroxy groups of any galactose moieties thereof to aldehydic groups and the thus-oxidized glycoprotein is then assayed for oxidized vicinal galactose moieties.

5. A method according to claim 4, wherein the galactose moieties are oxidized with galactose oxidase.

6. A method according to claim 4, performed simultaneously on a plurality of samples obtained from a plurality of individuals rectal mucus as part of a field screening for cancer.

7. A method according to claim 5, wherein the oxidized vicinal galactose moieties are visualized with basic fuchsin.

8. A method according to claim 1, wherein step (c) is conducted concurrently with step (b) on a different portion of the same mucus sample; and wherein immediately thereafter, when a negative result is obtained in both of steps (b) and (c), immediately thereafter another sample of rectal mucus is collected from the individual steps (a), (b) and (c) are repeated.

9. A method according to claim 8, wherein any aldehydic sugar moieties in a mucus sample further oxidized with periodic acid are visualized with basic fuchsin.

10. A method according to claim 1, wherein prior to the assaying thereof the rectal mucus sample is adsorbed onto a protein-capturing water-insoluble substrate and the substrate is then washed to remove the non-immobilized components of the mucus sample from the substrate; wherein the sample is assayed in step (a) by selectively oxidizing any glycoprotein in the sample so as to oxidize the primary hydroxy group of the galactose sugar moiety of any said carbohydrate therein to an aldehydic group and the thus-oxidized galactose moiety is then visualized with basic fuchsin; and wherein a mucus sample which tests negative in that assay is further oxidized with periodic acid and the aldehydic sugar moiety in the thus-oxidized sample is visualized with basic fuchsin.

11. A method according to claim 10, wherein the insoluble substrate is a membrane filter and wherein the galactose sugar moieties are oxidized with galactose oxidase.

12. A method according to claim 10, wherein the oxidizing agent for the galactose moieties is present in the insoluble substrate or is applied directly thereto after the mucus sample is applied thereto.

13. A method according to claim 12, wherein the insoluble substrate is a membrane filter, wherein the galactose sugar moieties are oxidized with galactose oxidase and wherein the galactose oxidase is applied directly to the membrane filter after the mucus sample is applied thereto.

14. A method of eliminating a false negative as a result of mucus sampling error in a rectal mucus method for screening for a cancerous or precancerous condition in a human being, which comprises conducting, within about a half hour period after collecting a sample of rectal mucus, the steps of (a) subjecting a first portion of the sample of rectal mucus in an assay for the presence therein of at least one marker carbohydrate selected from the group consisting of beta-D-Gal-(1->3)-D-Gal-NAc, Fuc-alpha-1->2 Gal-Beta(1->4)-Fuc-alpha-1->3-GlcNAc, Fuc-Alpha-1->2Gal-beta-(1->4)-Fuc-alpha-1->3-GlcNAc-beta-(1->3)-Gal-beta-(1>4)-GlcNAc and Fuc-alpha-1->2-Gal-beta-(1->4)-Fuc-alpha-1->3-GlcNA-beta-(1->3)-Gal-beta-(1->4)-Fuc-alpha-1->3-GlcNAc, and (b) either concurrently subjecting another portion of the same mucus sample or, if the first portion tests negative in step (a), thereafter subjecting the same portion, to oxidizing conditions which are capable of oxidative ring opening of the cyclic sugar moieties of any glycoprotein present in the sample at a hydroxy group-bearing ring carbon atom thereof to form aldehydic sugar moieties and then assaying the thus-oxidized sample for the presence therein of any aldehydic sugar moieties thus formed, the presence of thereby formed aldehydic sugar moieties confirming the adequacy of the mucus sampling and additionally, when the assay for marker carbohydrates is negative, that none of the marker carbohydrates are present in the mucus sample.

15. A method according to claim 14, wherein prior to the assaying thereof the rectal mucus sample is adsorbed onto a protein-capturing water-insoluble substrate and the substrate is then washed to remove the non-immobilized components of the mucus sample from the substrate; wherein a first portion of the sample is assayed for the marker carbohydrates by selectively oxidizing any glycoprotein in the sample with galactose oxidase so as to selectively oxidize the primary hydroxy groups of any galactose sugar moieties thereof to aldehydic sugar moieties; the thus-oxidized is then assayed for oxidized vicinal galactose moieties; and wherein a separate second portion of the rectal sample is concurrently oxidized in Step (b) with periodic acid and any of the cyclic sugar moieties in the thus-oxidized second portion of the sample are visualized with basic fuchsin.

16. In a process for producing an aqueous solution of basic fuchsin wherein a basic solution of fuchsin and sodium bisulfate is treated with activated charcoal and is stored at below room temperature, the improvement which comprises storing the basic solution at below room temperature until the color thereof fades to a straw color before the activated charcoal is added thereto, thereby rendering the solution storage-stable and enhancing its color development ability.

17. The process according to claim 16, wherein the solution is stored at about 0°–15° C. for at least one day.

18. The process according to claim 16, wherein the basic fuchsin solution is Schiff's Reagent.

19. A method for screening for a cancerous or precancerous condition in an organ other than the large intestine of a human being, which comprises subjecting a sample of proteinaceous secretion other than rectal mucus associated with that organ, to an assay for the presence therein of a marker carbohydrate selected from the group consisting of beta-D-Gal-(1->3)-D-Gal-NAc, Fuc-alpha-1->2 Gal-Beta(1->4)-Fuc-alpha-1->3-GlcNAc, Fuc-Alpha-1->2 Gal-beta-(1->4)-Fuc-alpha-1-22 3-GlcNAc-beta-(1->3)-Gal-beta-(1>4)-GlcNAc and Fuc-alpha-1->2-Gal-beta-(1->4)-Fuc-alpha-1->3-GlcNAc-beta-(1->3)Gal-beta-(1->4)-Fuc-alpha-1->3-GlcNAc.

20. A method according to claim 19, wherein prior thereto the proteinaceous secretion is adsorbed onto a protein-capturing water-insoluble substrate and the substrate is then washed to remove the nonimmobilized components of the mucus sample from the substrate; wherein the sample is assayed for the marker carbohydrates by selectively oxidizing any glycoprotein in the sample with galactose oxidase so as to selectively oxidize the primary hydroxy group of any galactose sugar moiety of any said marker carbohydrate therein to an aldehydic group and the thus-oxidized galactose moiety is then visualized with basic fuchsin; and wherein a portion of the sample which tests negative in that assay is further oxidized with periodic acid and the aldehydic sugar moiety in the thus-oxidized sample is visualized with basic fuchsin.

21. A method according to claim 20, which comprises the portion of the sample of proteinaceous secretion which is oxidized with periodic acid is a different portion of the same sample which is oxidized with galactose oxidase and is oxidized concurrently therewith.

22. The method of claim 19 wherein the human being is female and the fluid is vaginal or endocervical mucus.

23. The method of claim 19, wherein the human being is female and the secretion is discharge from a breast thereof.

24. The method of claim 19 wherein the human being is male and the fluid is prostatic secretion or semen.

25. The method of claim 19, wherein the human being is a patient exhibiting abnormal respiratory symptoms and the secretion is sputum.

* * * * *

UNITED STATES PATENT AND TRADEMARK OFFICE
CERTIFICATE OF CORRECTION

PATENT NO. : 5,348,860
DATED : September 20, 1994
INVENTOR(S) : Abulkalam M. SHAMSUDDIN It is certified that error appears in the above-indentified patent and that said Letters Patent is hereby corrected as shown below:

Claim 19, Column 14, Line 65: Delete "22" and insert

--›3--.

Signed and Sealed this

Thirty-first Day of January, 1995

Attest:

BRUCE LEHMAN

Attesting Officer     Commissioner of Patents and Trademarks